United States Patent
Shih

(10) Patent No.: US 7,371,369 B2
(45) Date of Patent: May 13, 2008

(54) POLYMERIC INTERPENETRATED NETWORK CARRIER AND SERIAL POLYMERIZATION INVOLVING A CROSSLINKED POLYMER NETWORK

(75) Inventor: Jenn S. Shih, Paramus, NJ (US)

(73) Assignee: ISP Investments Inc., Wilmington, DE (US)

( * ) Notice: Subject to any disclaimer, the term of this patent is extended or adjusted under 35 U.S.C. 154(b) by 491 days.

(21) Appl. No.: 10/705,691

(22) Filed: Nov. 10, 2003

(65) Prior Publication Data

US 2005/0101721 A1    May 12, 2005

(51) Int. Cl.
*C08J 3/00* (2006.01)
*A61K 31/74* (2006.01)

(52) U.S. Cl. .................. 424/78.02; 424/59; 523/351; 525/903

(58) Field of Classification Search ............ 424/78.02, 424/59; 523/351; 525/903
See application file for complete search history.

(56) References Cited

U.S. PATENT DOCUMENTS

| 4,833,222 | A | * | 5/1989 | Siddall et al. | 526/200 |
| 5,374,684 | A | * | 12/1994 | Tai | 525/254 |
| 5,814,031 | A | * | 9/1998 | Mooney et al. | 604/307 |

* cited by examiner

*Primary Examiner*—Kelechi C. Egwim
(74) *Attorney, Agent, or Firm*—Marilyn Maue; Walter Katz; William J. Davis

(57) ABSTRACT

This invention relates to a highly stable, dense interpenetrated crosslinked polymer network (ICPN) containing (a) a crosslinked, network-forming primary polymer containing vinyl lactam and/or acrylic acid moieties, and (b) a secondary, optionally crosslinked, distinctly different polymer interpenetrated into the network of (a) and derived from a monomer selected from the group consisting of an acrylate and/or acrylamide monomer. The invention also relates to the oil-suspension, sequential polymerization of (a) and (b) for producing the above described interpenetrated polymeric network.

12 Claims, No Drawings

POLYMERIC INTERPENETRATED NETWORK CARRIER AND SERIAL POLYMERIZATION INVOLVING A CROSSLINKED POLYMER NETWORK

BACKGROUND OF THE INVENTION

1. Field of the Invention

This invention relates to a polymeric concentrate which, when combined with water as a carrier for active pharmaceutical and/or cosmetic components, forms a gel or emulsion of improved stability and resistance to removal by water. The invention also relates to the process for obtaining said concentrate and carrier compositions.

2. Description of the Prior Art

U.S. Pat. Nos. 6,255,421 and 6,566,473 describe single stage, free radical polymerization processes which may involve one or more of the present monomers in an oil solution medium. These polymeric polymers are optionally crosslinked. However, these processes are designed to produce copolymers of graft, block, or random structure which do not provide entrapment of one polymer in the network of a distinctly different polymer. Similarly linear polymeric products are obtained by the bulk polymerization of long chain/short chain acrylate and/or acrylamide monomeric mixtures in oil medium, as described in U.S. patent application Ser. No. 10/350,404, filed on Jan. 23, 2003.

Current research is directed toward improving the stability of the prior polymeric systems and extending water insolubility and resistance to hinder rinse-off of water insoluble acrylate, acrylamide and acrylic polymeric carriers to provide more durable sun blocking compositions and other cosmetic or pharmaceutical formulations in the form of a more durable gel or emulsion carrier.

Accordingly, it is an object of this invention to achieve the above product goals together while providing an economical and commercially feasible process for producing such products.

Another object is to produce a polymer/oil carrier suitable for personal care or pharmaceutical formulations wherein the water resistant polymeric moieties are protected against rinse-off and to obviate the need for frequent applications, as with current sun block or other formulations.

Still another object is to produce a stable water resistant polymer/oil composition of comparatively dense structure for more securely holding active moieties in the carrier/active formulation.

Yet another object is to provide a water resistant polymer/oil carrier with enhanced ability to entrap a wide variety of water soluble and/or water insoluble chemical particles within its structure.

Another object is to provide a highly stable, liquid polymeric network as a carrier capable of containing relatively high loads of active component in a concentrate composition for impregnating pharmaceutical dressings and the like.

These and other objects and advantages of the invention will become apparent from the following description and disclosure.

SUMMARY OF THE INVENTION

In accordance with this invention there is provided a suitable oil based concentrate carrier for active materials comprising a highly stable water resistant network or web composed of a primary crosslinked polymer and a secondary polymer, of different structure, formed within the web of the primary polymer. The present concentrate carrier can be defined as an ICPN product which is produced by a sequential free radical suspension polymerization of the distinctly different monomers in an oil medium which, upon dilution with water, is capable of forming a stable gel or emulsion having skin and hair emollient properties.

In the following disclosure, the term "acrylate" is intended to include both unsubstituted acrylate and methacrylate species. Similarly, the term "acrylamide" is intended to include unsubstituted acrylamide and methacrylamide compounds and "acrylic" includes both acrylic and methacrylic species.

DETAILED DESCRIPTION OF THE INVENTION

The present physical incorporation of two or more structurally dissimilar polymers in an intricate web-like structure produces modifications of properties which impart extended stability, increased density and ability to entrap other chemical moieties in the structure of the copolymeric product while shielding them from easy rinse-off removal. In this invention, a secondary polymer is physically entrapped in the network of a primary crosslinked polymer to produce a highly stable, hydrogen bonded structure.

In accordance with the present invention, the ICPN product in oil comprises an intimate combination of at least two distinct polymer species in a network form wherein at least the web forming polymer is crosslinked up to 5 wt. %, preferably crosslinked between about 0.05 and 2 wt. %, with a suitable crosslinking agent. Unlike prior polymeric carrier compositions composed of chemical blends, block, graft or alternating polymer structures derived from the same monomeric components, the present polymer product involves no covalent bonds between the polymer species, thus extending carrier compatibility with a wide variety of active components. Since the pores of the network possess the ability to entrap other moieties, e.g. active pharmaceutical or cosmetic particles, the present polymer network permits higher loads of both water soluble and insoluble active components in a final product formulation, desirable for bandage and other impregnations.

The present ICPN products are produced under anhydrous conditions in a single reaction zone by sequential monomer polymerization in which the first stage consists of the free radical polymerization of a first monomer (A) with a crosslinking agent in a reaction medium of between about 25 and about 80 wt. % of a non-volatile oil at a temperature of from about 40° to about 160° C., preferably 50–150° C., for a period of about 1 to 12 hours and then, in a second stage of the suspension, polymerizing a distinctly different second monomer (B) in the presence of the same or a different free radical initiator, and optionally in the presence of a suitable crosslinking agent. The secondary monomer is dispersed in the oil reaction medium and polymerized at about the same temperature for an additional period of from about 2–12 hours. An effective crosslinking agent in a preferred amount of between about 0.05 and about 5 wt. % based on monomer A is introduced into the first stage of the process to provide the web-like polymer structure suitable for subsequent interpenetration of the second monomer B which forms a non-crosslinked or separately crosslinked polymer. Either monomer A alone or both of monomers A and/or B can be crosslinked during their sequential and respective stages of polymerizations in the first and/or second steps of the process. The crosslinking of monomer A in the first process stage is mandatory to provide a preformed network vehicle for interpenetration of the secondary polymer.

The selection of crosslinking agent is conventionally dependent on the monomer undergoing polymerization.

Suitable crosslinking agents include, but are not limited to, diallylimidazolidone, divinyl ether of diethylene glycol, pentaerythritol triallyl ether (PETE); pentaerythritol triacrylate (PETA); triallyl-1,3,5-triazine-2,4,6-(1H,3H,5H)trione (TATT), ethylene glycol diacrylate, 2,4,6-triallyloxy-1,3,5-triazine; N-vinyl-3-(E)-ethylidene-pyrrolidone (EVP), 1,7-octadiene, 1,9-decadiene, divinyl benzene, methylene-bis (methacrylamide), methylene-bis(acrylamide), N,N-divinylimidazolidone, ethylidene-bis(N-vinyl-pyrrolidone) (EBVP), hexaallyl sucrose or methylene bis((acrylamide).

Suitable A monomers for the sequential polymerization include, but are not limited to, N-vinylamides, dialkylaminoalkyl(meth)acrylates and vinyllactams in combination with a monomer whose polymer provides thickening properties such as acrylic and/or methacrylic acid monomers and/or sulfonate monomers. The vinyl lactam monomer A can also contain minor amounts of long chain and/or short chain alkyl acrylates and mixtures thereof. Specific examples of vinyl lactam and vinyl amides as monomer A include N-vinylpyrrolidone, N-vinylcaprolactam; and N-vinylformamide. Suitable B monomers include but are not limited to, vinyl acetate, styrene, vinyl esters, vinyl chloride, acrylamide or methacrylamide, an alkyl acrylate, alkyl methacrylate, an alkyl acrylamide, an alkylmethacrylamide, a hydroxyalkyl(meth)acrylate and a hydroxyalkyl(meth) acrylamide; an alkyl (polyethoxy)acrylate; an alkyl(polypropoxy)acrylate; an alkyl(poly-ethoxy-propoxy) acrylate, N,N-dialkylamino-alkyl(meth)acrylate; N,N-dialkyl aminoalkyl methacrylamide and their quaternized derivatives and mixtures thereof wherein the alkyl groups independently contain from 1 to 30 carbon atoms. Mixtures of short chain ($C_{1-8}$) and long chain ($C_{9-30}$) alkyl (meth)acrylates or alkyl (meth)acrylamides can also be employed as monomer B. Other suitable B monomers include comonomeric mixtures of the above species. Of the above A and B monomers, combinations of (A) poly(vinyl pyrrolidone/acrylic acid) with a long-chain, short-chain mixture of alkyl acrylates or vinyl caprolactam/acrylic acid with an alkyl acrylate and/or acrylamide are preferred.

The most preferred process involves polymerizing and crosslinking A monomer, e.g. vinyl pyrrolidone or vinyl prrolidone mixture in the first stage of the process, followed by the polymerization of monomer B in the second stage. It will be understood that monomer B can comprise a mixture of 2 to 3 polymerizable monomers for dispersement in the preformed crosslinked polymer system. In general, the weight ratio of monomer A to monomer B can vary between about 1:10 and about 10:1, preferably between about 1:2 and about 2:1. The medium employed for the polymerization reactions is a non-volatile oil, desirably a cosmetically or pharmaceutically acceptable oil such as a vegetable oil, e.g. castor oil, vernonia oil, olvie oil; a mineral oil, water insoluble esters, e.g. isopropyl-palmitate or myristate, isocetyl stearate, and the like. Non-volatile silicone oils such as, for example polyalkyl siloxanes, polyaryl siloxanes, polyalkylaryl siloxanes and polyether siloxane copolymers; and non-volatile silicones such as cyclomethicones also may be used.

Non-volatile polyalkylsiloxanes include, for example, polydimethylsiloxanes (Dimethicone) with viscosities ranging from about 5 to about 600,000 centistokes (cS) at 25° C. These siloxanes are available, for example, from the General Electric Company as the VISCASIL series and from Dow Corning as the Dow Corning 200 products. Their viscosity can be measured by the glass capillary viscometer procedure set forth in Dow Corning Corporate Test Method CTM 0004 issued Jul. 20, 1970. Preferably, the viscosity of these siloxanes selected have a viscosity of about 100 to about 100,000 cS, and most preferably, a viscosity of up to about 15,000 cS.

Suitable non-volatile polyalkylaryl siloxanes include, for example, poly(methylphenyl)siloxanes having viscosities of about 15 to 65 cS at 25° C. These siloxanes are available, for example, from the General Electric as SF 1075 methylphenyl fluid or from Dow Corning as 556 Cosmetic Grade Fluid. Additionally, poly(dimethylsiloxane)-(diphenylsiloxane) copolymers having a viscosity in the range of about 10 to 100,000 cS at 25° C. are useful.

These and other suitable silicones are disclosed in U.S. Pat. Nos. 2,826,551, 3,964,500 and 4,364,837.

Other suitable oils for use herein include cosmetically or pharmaceutically acceptable materials such as mixtures of light and heavy mineral oils, and water-insoluble organic esters such as isopropyl palmitate and isopropyl myristate, isocetyl stearate and isocetyl palmitate.

Conventional free radical initiators are employed in both the first and second stages of the reaction; although peroxy type initiators are preferred. Particularly preferred is tertiary butyl peroxy pivalate. Other initiators include but are not limited to benzoyl peroxide, lauryl peroxide, tertiary amyl peroxy pivalate, percarbonates such as dicyclo hexyl peroxy dicarbonate and azo compounds such as 2,2-azo-bis(isobutyronitrile), 2,2-azo-bis(2,4-dimethyl-valeronitrile, 2,2-azo-bis(cyanocyclohexane and mixtures of the foregoing compounds.

The density of the present ICPN product is substantially greater than that of the corresponding block, graft or random copolymers employing the same amounts of the same monomers.

In general the molecular weight and viscosity of instant ICPN polymer can be controlled by limiting the degree of crosslinking and/or polymerization of either the network forming polymer or the polymer presented for entrapment.

A particular advantage of the present ICPN product is that the structure provides a greater degree of flexibility in viscosities currently required for particular uses. In general, the viscosity of the present carrier composition is between about 1,000 and about 500,000, preferably 10,000–100,000, centistokes at 25° C.

Optional components which may be included in the first or second stage of the polymerization reactions or in the subsequent formulation with the active cosmetic or pharmaceutical component include up to about 5 wt. % of a dispersant, a thickener, a moisturizer or other modifier depending upon the use of the final formulation.

The present concentrate carrier has a solids content of between about 10 and about 60%, preferably 20–50%.

Active components subsequently added to the ICPN carrier are any of the conventional insecticides, fungicides, pesticides, UV blocking agents, hair or skin conditioning agents, bleaching agents, pharmaceutical agents, eg. drugs, and the like.

The present carriers in the oil suspension are conveniently converted into emulsions or emulsified hydrogels which contain the polymer network in the aqueous phase. When the product of the serial polymerization process is acidic and an emulsion is desired, it can be mixed with an organic or inorganic base before dilution with water. The oil phase consists of the oil used during polymerization. The emulsions can be a water-in-oil (w/o), oil-in-water (o/w), or mixed type (w/o/w). When a proportionately higher amount of the crosslinked polymer is present, the aqueous phase has attributes of a swollen crosslinked hydrogel. The hydrogel phase can be either dispersed in oil as fine gel particles (w/o), or the oil droplets can be dispersed in a continuous hydrogel phase (o/w).

The selected ratios of oil-to-water in such emulsions and emulsified hydrogels are predetermined by the desired use compositions; these can be adjusted within a broad range. Typically, oil-to-water ratios reside in the range of about 30:70 to about 10:90 by volume in the case of o/w emulsions and emulsified hydrogels. In corresponding w/o systems, the ratios of oil-to-water are suitably in the range of about 90:10 to about 30:70 by volume. Typically, when there is a need for a significant amount of oil in the final emulsion, the reaction product, that is, the slurry of polymer in oil, is directly converted into an emulsion or an emulsified hydrogel by addition of a calculated amount of water. When, however, the ratio of oil-to-water in the emulsion is desired to be low, the emulsion is made using the filtered reaction product that consists of polymer powder swollen with the absorbed oil.

When an o/w system is desired, the reaction product is gradually added to water, whereas when a w/o system is desired, water is added gradually to the reaction product, with appropriate rapid agitation or homogenization. Suitable surfactants up to about 5 wt. %, can be added to these systems. Conventional surfactants, such as, for example, Tween® 20, 21, 40, 61 (ICI) or Igepal® CO-630 (product of Rhone-Poulenc), for o/w emulsions and emulsified hydrogels; and Span® 60, 65, 80, 85 (ICI) for w/o systems, are suitably employed. The surfactant added optionally to the polymerization reaction mixture also may be sufficient to form the desired emulsion or emulsified hydrogel.

Reference is now had to the following examples which illustrate preferred embodiments, but are not to be construed as limiting to the scope of the invention as more properly defined in the appended claims.

EXAMPLE 1

Into a 1-liter, four-necked glass kettle, equipped with 2 feeding pumps an anchor agitator, a thermocouple and a condenser, was charged 600 g of CERAPHYL 494 (iso-cetyl stearate) and heated to 65° C. for 30 minutes. The solution was purged with nitrogen throughout the ensuing reaction process. Solution I of 80 g of N-vinylpyrrolidone mixed with 2.4 g of pentaerythritol triallyl ether (PETE) and solution II of 80 g of acrylic acid were separately prepared and solutions I and II, as well as 0.5 g of t-butylperoxypivalate initiator were added to the kettle over a 4 hour interval. Solutions I and II were introduced at a constant feeding rate and held at 65° C. for 1 hour and then heated to 80° C. Four times every 2 hours, 0.2 g of the initiator was added and the resulting solution was held at 80° C. for 2 additional hours after the last initiator charge. The resulting crosslinked polymer suspension was then cooled to 65° C. and a mixture of 32 g of methyl methacrylate, 80 g of butyl methacrylate and 48 g of stearyl methacrylate was gradually introduced over a period of 2 hours. The resulting solution was held at 65° C. for 1 hour before raising the temperature to 80° C. T-butylperoxypivalate (0.2 g) was added 5 times every 2 hours. The resulting solution containing the polymeric, crosslinked vinyl pyrrolidone polymer network penetrated with the polymeric acrylate mixture was held for an additional 2 hours after which 2.0 g of water was added and stirred for another 5 hours at 80° C. and then cooled and a homogenized product was recovered.

EXAMPLE 2

Into a 1-liter, four-necked glass kettle, equipped with 2 feeding pumps an anchor agitator, a thermocouple and a condenser, was charged 600 g of CERAPHYL 494 (iso-cetyl stearate) and heated to 65° C. for 30 minutes. The solution was purged with nitrogen throughout the ensuing reaction process. Solution I of 80 g of N-vinylpyrrolidone mixed with 2.4 g of pentaerythritol triallyl ether (PETE) and solution II of 80 g of acrylic acid were separately prepared and solutions I and II, as well as 0.5 g of t-butylperoxypivalate initiator were added to the kettle over a 4 hour interval. Solutions I and II were introduced at a constant feeding rate and held at 65° C. for 1 hour and then heated to 80° C. Four times every 2 hours, 0.2 g of the initiator was added and the resulting solution was held at 80° C. for 2 additional hours after the last initiator charge. The resulting crosslinked polymer suspension was then cooled to 65° C. and a mixture of 32 g of methyl methacrylate, 80 g of butyl methacrylate, 48 g of stearyl methacrylate and 0.3 g PETE was gradually introduced over a period of 2 hours. The resulting solution was held at 65° C. for 1 hour before raising the temperature to 80° C. T-butylperoxypivalate (0.2 g) was added 5 times every 2 hours. The resulting solution containing the polymeric, crosslinked vinyl pyrrolidone polymer network penetrated with the crosslinked polymeric acrylate mixture was held for an additional 2 hours after which 2.0 g of water was added and stirred for another 5 hours at 80° C. and then cooled and a homogenized product was recovered.

EXAMPLE 3

Into a 1-liter, four-necked glass kettle, equipped with 2 feeding pumps an anchor agitator, a thermocouple and a condenser, was charged 540 g of CERAPHYL 494 (iso-cetyl stearate) and 60 g of hexylene glycol and heated to 65° C. for 30 minutes. The solution was purged with nitrogen throughout the ensuing reaction process. Solution I of 140 g of N-vinylpyrrolidone and 35 g of stearyl methacrylate mixed with 1.3 g of pentaerythritol triallyl ether (PETE) and solution II of 58 g of acrylic acid were separately prepared and solutions I and II, as well as 0.5 g of t-butylperoxypivalate initiator were added to the kettle over a 4 hour interval. Solutions I and II were introduced at a constant feeding rate and held at 65° C. for 1 hour and then heated to 90° C. Five times every 2 hours, 0.2 g of the initiator was added and the resulting solution was held at 90° C. for 2 additional hours after the last initiator charge. The resulting crosslinked polymer suspension was then cooled to 65° C. and a mixture of 32 g of methyl methacrylate, 80 g of butyl methacrylate, 48 g of stearyl methacrylate and 0.3 g PETE was gradually introduced over a period of 2 hours. The resulting solution was held at 65° C. for 1 hour before raising the temperature to 80° C. T-butylperoxypivalate (0.2 g) was added 5 times every 2 hours. The resulting solution containing the polymeric, crosslinked vinyl pyrrolidone polymer network penetrated with the crosslinked polymeric acrylate mixture was held for an additional 2 hours after which 2.0 g of water was added and stirred for another 5 hours at 100° C. and then cooled and a homogenized product was recovered.

EXAMPLE 4

Into a 1-liter, four-necked glass kettle, equipped with 2 feeding pumps an anchor agitator, a thermocouple and a condenser, was charged 300 g of CERAPHYL 494 (iso-cetyl stearate) and 60 g of hexylene glycol and heated to 65° C. for 30 minutes. The solution was purged with nitrogen throughout the ensuing reaction process. T-butylperoxypivalate was added as well as a mixture of 15 g of methyl methacrylate, 36.75 g of butyl methacrylate, 32.25 of stearyl methacrylate and 0.2 g PETE was added to the kettle over a period of 3 hours. The resulting solution was held at 65° C. for 1 hour and then heated to 90° C. Five times every 2 hours, 0.1 g of the initiator was added and the resulting solution was held at 90° C. for 2 additional hours after the last initiator charge. The resulting crosslinked acrylate polymer mixture was then cooled to 65° C. and Solution I of 50 g of vinylpyrrolidone and Solution II of 50 g of acrylic acid were prepared and fed into the kettle at a constasnt rate over a 4 hour period. The resulting solution was held at 65° C. for 1 hour before raising the temperature to 80° C. T-butylperoxypivalate (0.1 g) was added 4 times every 2 hours. The resulting solution containing the polymeric, crosslinked methacrylate polymer network penetrated with the vinyl pyrrolidone polymer was held for an additional 2 hours after which 1 g of water was added and stirred for another 5 hours at 100° C. and then cooled and a homogenized product was recovered.

EXAMPLE 5

In a 4 oz glass jar, 3.0 grams of the product of Example 1, 7 g of ethylhexylmethoxycinnamate (Escalol 557 from ISP), 2 g of benzophenone-3 (Escalol 567 from ISP), 3 g of ethylhexyl salicylate (Escalol 587 from ISP), and 4 g of isocetyl stearate solvent (Ceraphyl 494 from ISP) was stirred until a uniform mixture was obtained. Then 0.62 g of 2-amino-2-propanol neutralizer and 80.38 g of distilled water were added and stirred for a period of 1 hour. The resulting sunblock creamy lotion had a Brookfield viscosity of 30,000 cps and exhibited skin moisturizing properties.

What is claimed is:

1. A stable, water resistant, anhydrous interpolymeric carrier concentrate which is an interpenetrated crosslinked polymer network for an active component comprising (a) a non-volatile oil suspension medium, (b) an oil soluble secondary polymer derived from a $C_1$ to $C_{30}$ alkyl acrylate monomer or a mixture of said acrylates formed and physically entrapped in a primary network of (c) a water insoluble, crosslinked polymer derived from vinyl pyrrolidone and acrylic acid monomers, or including an alkyl acrylate and alkyl acrylamide.

2. The carrier concentrate of claim 1 wherein the weight ratio of (b) to (c) is between about 10:1 and 1:10.

3. The carrier concentrate of claim 2 wherein the weight ratio of (b) to (c) is between about 2:1 and 1:2.

4. The carrier concentrate of claim 1 wherein (a) said oil is an organic suspension agent.

5. The carrier concentrate of claim 4 wherein said oil is isocetyl stearate.

6. The carrier concentrate of claim 1 wherein (c) is crosslinked between about 0.5–5 wt. %.

7. The carrier concentrate of claim 1 wherein (c) is crosslinked with pentaerithritol triallyl ether.

8. The carrier concentrate of claim 1 which contains a surfactant and/or a dispersant in an effective distributing amount for the active component.

9. The carrier concentrate of claim 1 wherein an active cosmetic or pharmaceutical component is added to the carrier concentrate in an amount up to about 20 wt. % and said concentrate optionally contains less than 10 wt. % of an inert excipient selected from the group consisting of a thickener, a moisturizer, a dispersing agent or a mixture thereof.

10. The carrier concentrate of claim 9 wherein said active component is a sun blocking agent.

11. The carrier concentrate of claim 1 wherein the weight ratio of monomer in polymer (c) to the monomer in polymer (b) is between about 1:10 and about 10:1.

12. The carrier concentrate of claim 1 wherein the weight ratio of monomer in polymer (c) to the monomer in polymer (b) is between about 1:2 and about 2:1.

* * * * *